(12) United States Patent
Torchilin et al.

(10) Patent No.: US 6,203,775 B1
(45) Date of Patent: Mar. 20, 2001

(54) CHELATING POLYMERS FOR LABELING OF PROTEINS

(75) Inventors: Vladimir P. Torchilin, Charleston; Vladimir S. Trubetskoy, Milton, both of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/034,912

(22) Filed: Mar. 19, 1993

(51) Int. Cl.[7] .......................... A61K 51/00; A61M 36/14
(52) U.S. Cl. ................. 424/1.69; 530/391.3; 530/391.9; 530/391.7; 530/391.5; 424/1.11
(58) Field of Search .............................. 424/1.11, 9, 85.8, 424/85.91, 1.41, 1.45, 1.53, 1.57, 1.69, 9.34; 534/10, 14, 15, 16; 530/391.3, 391.5, 391.7, 391.9

(56) References Cited

U.S. PATENT DOCUMENTS

| | | | |
|---|---|---|---|
| 4,732,864 | * | 3/1988 | Tolman ................................. 436/547 |
| 4,732,974 | * | 3/1988 | Nicolotti et al. . | |
| 5,057,313 | * | 10/1991 | Shih et al. ........................ 424/85.91 |
| 5,059,541 | * | 10/1991 | Fritzberg et al. ..................... 436/501 |
| 5,091,514 | * | 2/1992 | Fritzberg et al. ....................... 534/14 |
| 5,155,215 | * | 10/1992 | Ranney ................................. 534/16 |
| 5,162,505 | * | 11/1992 | Dean et al. ........................ 530/391.5 |
| 5,175,343 | * | 12/1992 | Fritzberg et al. . | |
| 5,230,883 | * | 7/1993 | Kornguth et al. ........................ 424/9 |
| 5,242,679 | * | 9/1993 | Fritzberg et al. ..................... 424/1.1 |
| 5,252,317 | * | 10/1993 | Keana ..................................... 424/9 |
| 5,302,370 | * | 4/1994 | Neumeier et al. .................. 424/1.53 |
| 5,338,532 | * | 8/1994 | Tomalia et al. ..................... 424/1.49 |
| 5,364,613 | * | 11/1994 | Siering et al. ............................ 424/9 |
| 5,364,614 | * | 11/1994 | Platzek et al. ........................... 424/9 |
| 5,385,719 | * | 1/1995 | Unger et al. ......................... 528/272 |
| 5,549,883 | * | 8/1996 | Srinivasan et al. ................. 424/1.45 |

FOREIGN PATENT DOCUMENTS

PCT/US94/
03015 * 5/1994 (WO) .

OTHER PUBLICATIONS

Fritzberg, A.R., "Specific and stable labeling of antibodies with technetium–99m with a diamide dithiolate chelating agent", Proc. Natl. Acad Sci, USA, vol. 8, pp. 4025–4029, Jun. 1988.

Griffiths, G.L., "Radiolabeling of Monoclonal Antibodies and Fragments with Technetium and Rhenium", Biconjugate Chem., vol. 3, No. 2, pp. 91–92, 1992.

Goldenberg, D.M., "Clinical Studies of Cancer Radioimmunodetection with Carcinoembryonic Antigen Monoclonal Antibody Fragments Labeled with 123I or 99mTC1", Cancer Research (Suppl.) vol. 50, pp. 909s–921s, 1990.

Hansen, H.J., "Preclinical Evaluation of an "Instant" 99mTc–labeling Kit for Antibody Imaging1", Cancer Research (Suppl.), vol. 30, pp. 794s–798s, 1990.

Eary, Janet F., "Successful Imaging of Malignant Melanoma with Technetium–99m–Labeled Monoclonal Antibodies" The Journal of Nuclear Medicine, vol. 30, No. 1, Jan. 1989.

Abrams, M.J., "Technetium–99m–Human Polyclonal IgG Radiolabeled via the Hydrazino Nicotinamide Derivative for Imaging Focal Sites of Infection in Rats", The Journal of Nuclear Medicine, vol. 31, No. 12, 1990.

* cited by examiner

*Primary Examiner*—José G. Dees
*Assistant Examiner*—Dameron Jones
(74) *Attorney, Agent, or Firm*—Fish & Richardson P.C.

(57) ABSTRACT

A method of labelling a protein with a metal involving chelating a metal to a compound, with a molecular weight of at least 1,000, and a reactive group capable of forming a covalent bond with a target protein, and conjugating the metallically-labelled compound to a protein.

36 Claims, 6 Drawing Sheets

CHELATING POLYMERS FOR LABELING OF PROTEINS

BACKGROUND OF THE INVENTION

The field of the invention is protein labelling.

An important issue in clinical radiology is the labelling of proteins, such as monoclonal antibodies, for diagnostic and therapeutic purposes. The radioactive metals, indium ($^{111}$-In) and technetium ($^{99m}$Tc) are useful for diagnostic imaging, whereas rhenium ($^{186\ and\ 188}$-Re) is useful for targeted tumor therapy.

SUMMARY OF THE INVENTION

A problem with $^{99m}$-Tc and $^{186\ Or\ 188}$-Re labeling is the non-specific incorporation of chemically-reduced metal into the protein; the reduced metal is associated with a large number of low-affinity binding sites on the protein. Upon injection into the bloodstream of a patient, this weakly-bound metal can detach from the protein and bind to non-target tissues. The non-specifically-bound metal complicates the detection of target-bound metal by increasing biological background counts, the chance for artifacts, and the time necessary to obtain accurate target/non-target discrimination.

The invention addresses this problem by providing a method of labelling proteins, in particular with binding specificity for cell surface molecules, with a metal, such as a radioisotope or a paramagnetic metal, by first chelating the metal to a compound having a molecular weight of at least 1,000. The protein is then labelled by reacting the labelled compound, which contains a first reactive group capable of forming a covalent bond with a protein, with the protein, which contains or is modified to contain a second reactive group, forming a covalent bond between the first and second reactive groups.

The compound is preferably a polymer such as a polypeptide, e.g., poly-L-lysine.

The reactive group of the chelating compound is preferably one that forms a covalent bond with a sulfhydryl group on the protein, such as a maleimido group.

Preferably, the protein to be labelled is an antibody, more preferably a monoclonal antibody and most preferably, the Fab' fragment of a monoclonal antibody.

The method of the invention results in the formation of a metal-labelled protein that is substantially devoid of unchelated metal. By making use of a compound with a molecular weight of at least 1,000, the method of the invention provides a way to amplify the specific activity of the labelled protein by chelating multiple atoms of metal to the compound prior to conjugating the chelating compound to the target protein. Another advantage this method is the ability to easily purify the high molecular weight chelated compound from the very low molecular weight unchelated metal.

The labelled protein of the invention, which specifically binds to certain mammalian cells, can be used in diagnostic methods for labelling cells in a mammal. For detection, the metal is preferably a paramagnetic metal such as gadolinium (Gd), or a radioisotope such as $^{111}$-In or $^{99m}$-Tc.

Certain labelled proteins of the invention, which specifically bind to certain mammalian cells, can be used for killing unwanted cells, such a tumor cells, in a mammal. For radiotherapy, the metal is preferably a cytotoxic radioisotope, such as $^{186}$-Re or $^{188}$-Re.

Other features and advantages of the invention will be apparent form the following detailed description, and from the claims.

DETAILED DESCRIPTION

The drawings are first briefly described. Drawings

COMPLEXES OF THE INVENTION

Figure 1:
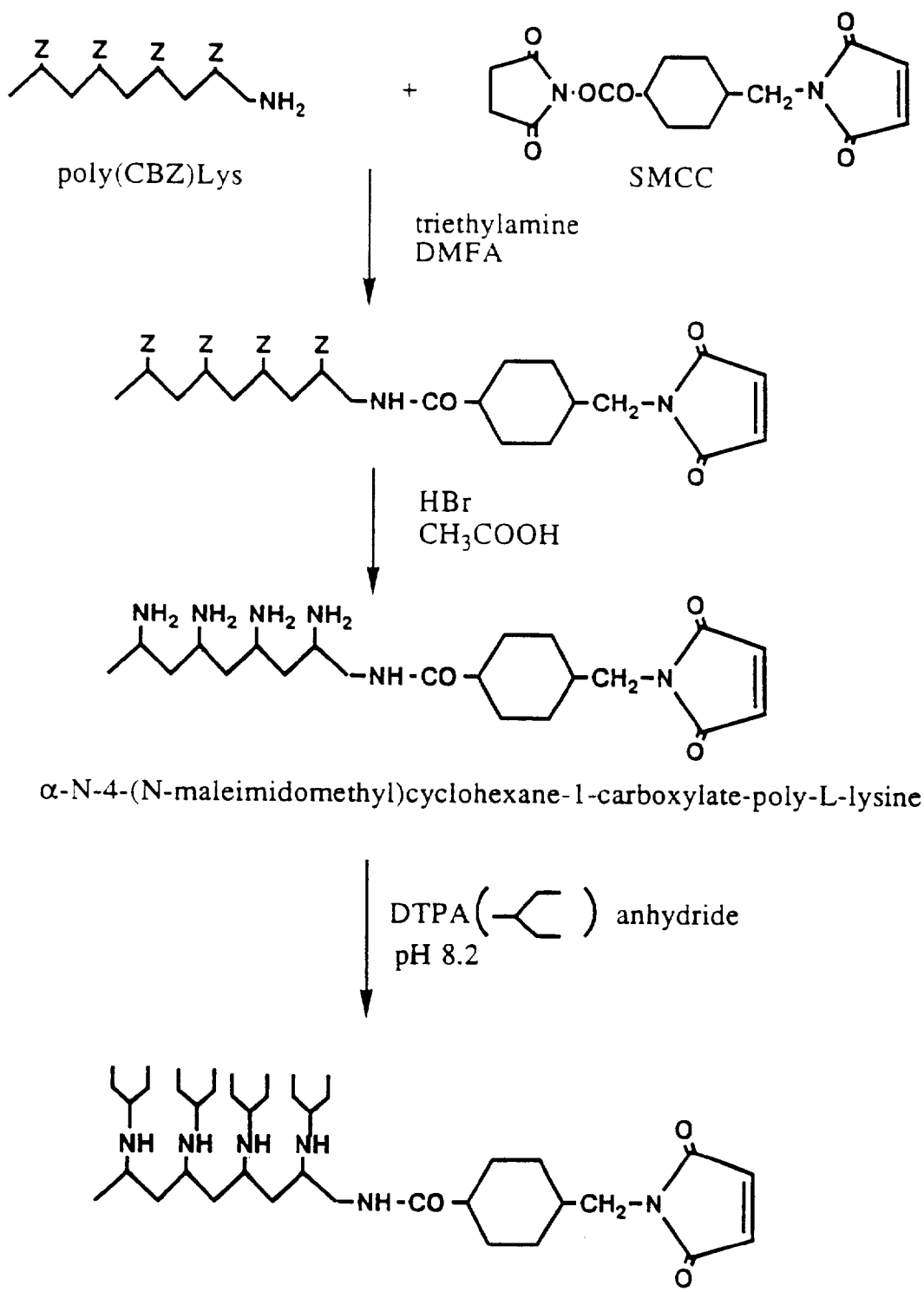
FIG. 1 is a diagram illustrating the synthesis of N-terminal maleimido poly-L-lysine-DTPA.

As is described in the Summary above, the methods and composition of the invention employ several components, which will now be discussed in greater detail.

The starting compound, designed to be preloaded with a metal, can be any compound, such as a polymer, with a molecular mass of at least 1,000 daltons, capable of being modified to chelate metals and bind to proteins. Any naturally-occurring or synthetically-made polymer, such as a polysaccharide, containing a reactive group capable of forming a covalent bond with a protein and more than one chelating group can be used. A polypeptide, such a poly-L-lysine, or a any peptide or protein that is naturally occurring or synthetically-made can also be used.

The first reactive group of the compound is instrumental in forming a covalent bond to a target protein. This group can be a thiol-reactive group, forming a thioester bond with a sulfhydryl group of a protein. The compound can be modified with reagents, such as SPDP or SMCC, to add a single terminal thiol-reactive group, such as PDP or MCC, respectively.

The protein to be labelled can be any protein or glycoprotein that specifically binds to a given cell, such as an antibody. The invention can employ not only intact monoclonal or polyclonal antibodies, but also an immunologically-active antibody fragment, for example, a Fab' or (Fab')$_2$ fragment; an antibody heavy chain, an antibody light chain; a genetically engineered single-chain Fv molecule (Ladner et al., U.S. Pat. No. 4,946,778); or a chimeric antibody, for example, an antibody which contains the binding specificity of a murine antibody, but in which the remaining portions are of human origin. Cell receptor-specific ligands, e.g., a cytokine such as interleukin-2, can also be labelled according to the invention.

The second reactive group is a component of the target protein. As described above, the second reactive group can be a free sulfhydryl group that is naturally occurring or is the result of chemical modification of the target protein. To generate a free sulfhydryl group of an antibody molecule, the antibody can be enzymatically cleaved with pepsin to yield (Fab')$_2$ fragments, which are then gently reduced with DTT or 2-mercaptoethanol to yield free sulfhydryl group-containing Fab' fragments. Proteins can also be chemically modified by standard techniques to add a sulfhydryl group. For example, Traut's Reagent (2-Iminothiolane-HCl) can be used to introduce a sulfhydryl group on primary amines, such as lysine residues or N-terminal amines of the target protein. The chelating group of the compound can be any chelating group that can be introduced into the compound. For example, the compound can be treated with DTPA to introduce multiple chelating groups into a polypeptide via primary amines. The method of the invention provides a way to amplify the specific activity of the labelled protein by chelating multiple atoms of metal to the compound prior to conjugating the chelating compound to the target protein. Other suitable chelating groups are known in the art, e.g., triethylenetetramine-hexaacetic acid, ethylenediamine-tetraacetic acid, 1,2-diaminocyclohexane-N,N,N',N'-tetra-acetic acid, N,N'-Di(2-hydroxybenzyl) ethylenediamine, N-(2-hydroxyethyl)ethylenediaminetriacetic acid, nitrilotri-acetic acid, ethylene-bis(oxyethylene-nitrilo) tetraacetic acid, 1,4,7,10,-tetraazacyclodo-decane-N,N',N'',N'''-tetraacetic acid, 1,4,7,10,-tetraaza-cyclododecane-N,N',N'',-triacetic acid, 1,4,7-tris(carboxymethyl)-10-(2'-hydroxy) propyl)-1,4,7,10-tetraazocyclodecane, 1,4,7-triazacyclonane-N,N',N''-triacetic acid, or 1,4,8,11-tetraazacyclotetradecane-N,N',N'',N'''-tetra-acetic acid.

Any metal that can be incorporated into the compound via the chelating groups can be used to label the target protein. For example, labelling proteins with the a paramagnetic metal is useful in magnetic resonance imaging (MRI). The paramagnetic element may be chosen from the group of transitional metals or lanthanides having atomic numbers 21–29, 42, 44, or 57–71. The paramagnetic metal may be, e.g., gadolinium (III), dysprosium (III), holmium (III), europium (III), iron (III), or manganese (II).

Radioactive metals, such as $^{111}$-In and $^{99m}$-Tc, can also be chelated to the compound for the labelling of mammalian cells for diagnostic purposes. Radioactive metals that are cytotoxic, such as $^{186\ or\ 188}$-Re, can be chelated to the compound for use as a radiotherapeutic designed to kill unwanted mammalian cells, such a tumor cells. Other useful radioisotopes are known in the art, e.g., copper ($^{67}$-Cu), yttrium ($^{90}$-Y), bismuth ($^{212}$-Bi), and lutetium ($^{177}$-Lu).

Diagnostic Method

The labelled protein of the invention can be used to label mammalian cells that contain or bear on their surface a molecule that specifically binds to the labelled protein. The labelled protein can be administered to an animal, e.g., a human patient, by conventional methods, e.g. in a pharmaceutically acceptable carrier, such as physiological saline. The labelled protein can be administered intravenously, intraperitoneally, subcutaneously or intramuscularly at a dosages of approximately 0.01–10 mCi/kg of body weight.

Cells labelled with a protein labelled with the metal, Gd, can be detected using standard magnetic resonance imaging (MRI) techniques. Cells labelled with protein labelled with the radioisotopes, $^{111}$-In or $^{99m}$-Tc, can be detected using a gamma-radiation detection system, such as a gamma-camera.

Radiotherapy

Labelled proteins of the invention, which contain a cytotoxic metal such as a lethal radioisotope, can be used to kill mammalian cells that contain or bear on their surface a molecule that specifically binds to the labelled protein. To destroy unwanted cells in a mammal, proteins labelled with a cytotoxic radioisotope, such as $^{186\ or\ 188}$-Re, can be administered to the patient as described above. In this manner, the cytotoxic radiation is localized to the cells that have specifically bound the labelled protein. Unwanted cells, such as tumor cells, can be killed by bound protein labelled with radioisotopes, such as $^{186\ or\ 188}$-Re. For radiotherapeutic purposes, a dose range of approximately 1–250 mCi/injection per patient can be used.

EXAMPLE 1

Antibody-Chelating Polymer Conjugates

The following chemicals are purchased from SIGMA Chemical Company, St. Louis, Mo.: Poly-L-lysine (PLL), carbobenzoxy-PLL (CBZ-PLL), N-succinimidyl (2-pyrididldithio) propionate (SPDP), succinimidyl maleidomethyl cyclohexane carboxylate (SMCC), and diethylene triamine pentaacetic acid (DTPA). All radioisotopes are purchased from New England Nuclear, Billerica, Mass.

Figure 2:
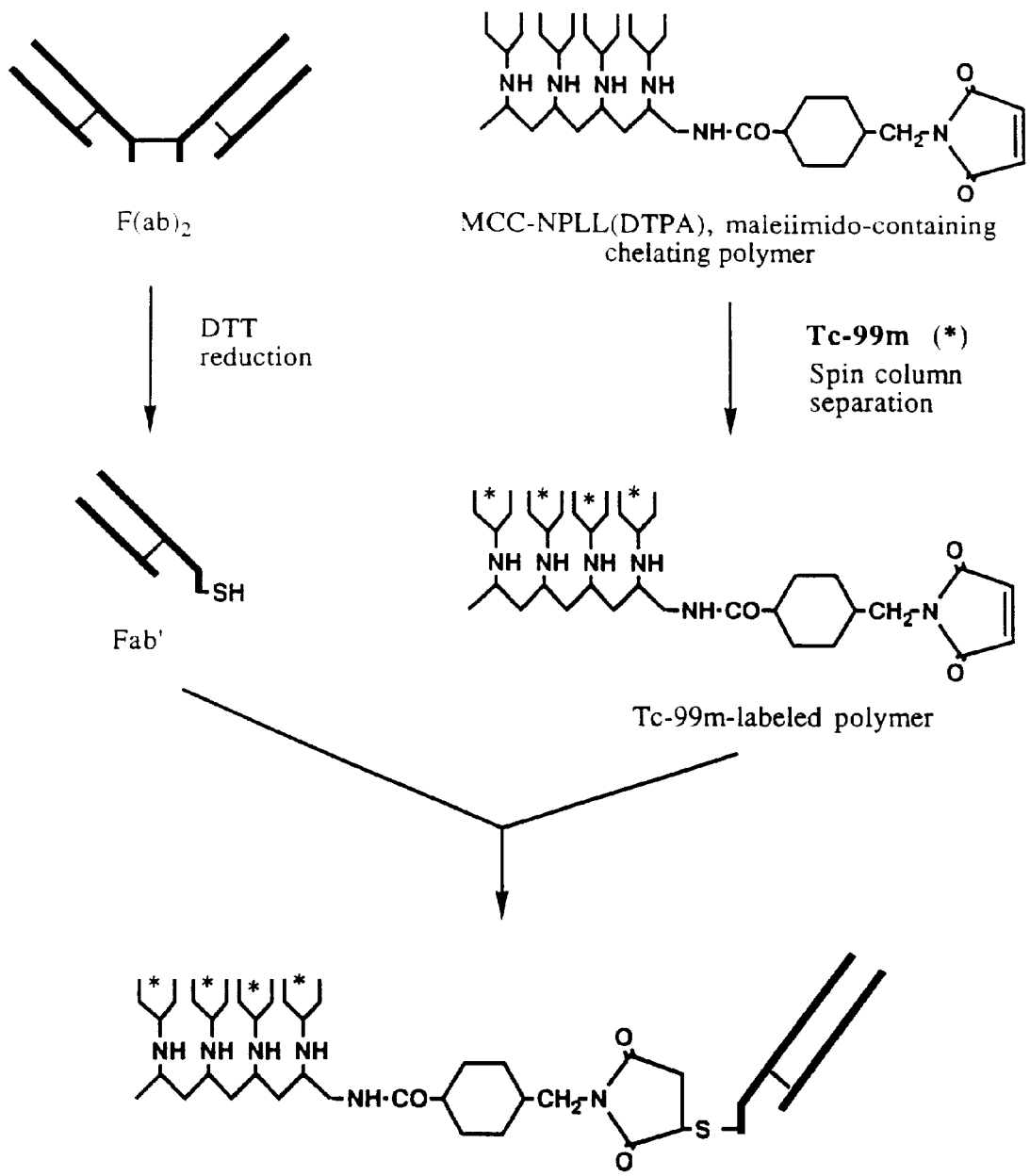
FIG. 2 is a diagram illustrating the synthesis of Fab'-NPLL (DTPA) conjugate labelled with $^{99m}$-Tc.

The procedure for synthesizing chelating polymers is shown in FIG. 1 and FIG. 2. The polymer was first reacted with SMCC to add a maleimido group, followed by the addition of single terminal chelating groups, such as PDP or MCC, or numerous chelating groups using DTPA.

Figure 3:
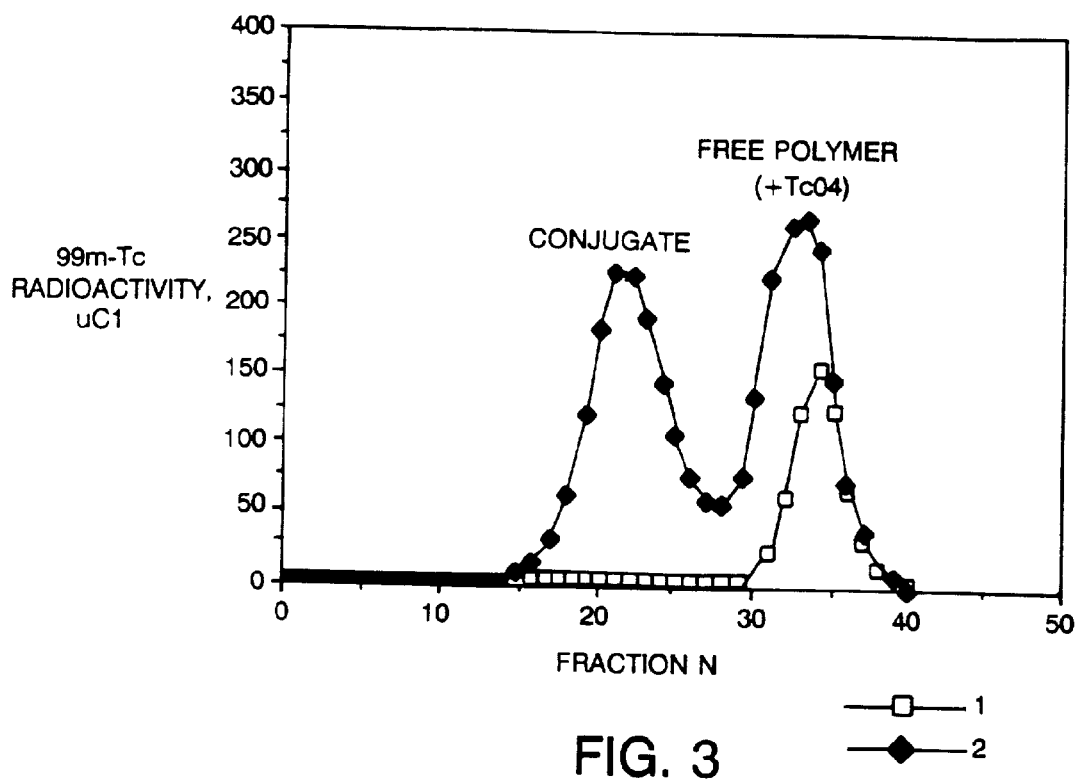
FIG. 3 is a graph showing the chromatographic analyis of free TcO$_4^-$ and reaction mixture after R11D10 Fab' conjugation with $^{99m}$-Tc-labelled DTPA-PLL.

The chelating polymers obtained were loaded with radioisotopes, such as $^{111}$-In, $^{99m}$-Tc or $^{186}$-Re. $^{111}$-In labelling was performed by transchelation of the metal from its complex with citrate. $^{99m}$-Tc or $^{186\ or\ 188}$-Re labelling was performed by chelating these radioisotopes upon their reduction from $MeO_4^-$ ions into $Me^{3+}$ by $SnCl_2$ in acidic medium. Since the chelating polymer is of relatively high molecular weight, Sephadex G-10 spin cartridges or conventional chromatography on BioGel 0.5 m (BIORAD Laboratories, Richmond, Calif.) were used to separate labelled polymers from unbound radioisotope. Radioactive labelling of the chelating polymer and subsequent conjugation to antibody is shown in FIG. 3.

Figure 4:
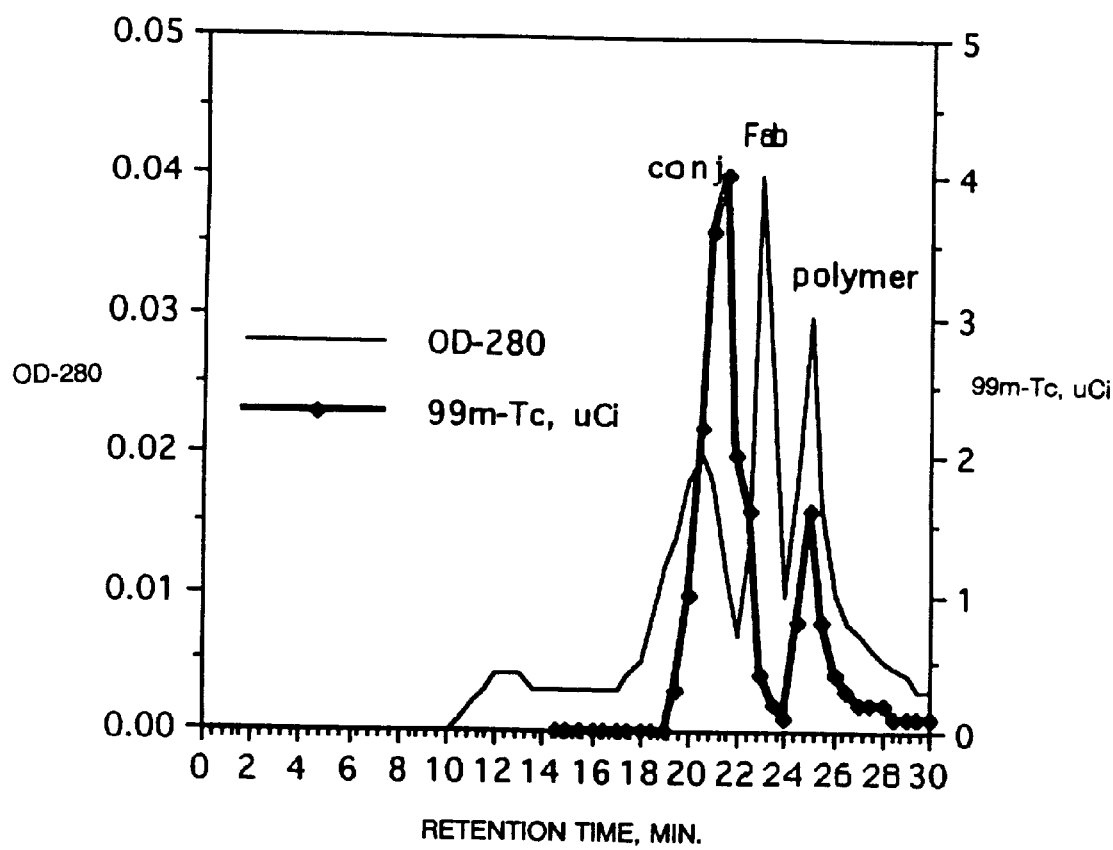
FIG. 4 is a graph showing HPLC analysis of the reaction mixture from the R11D10 Fab' conjugation with $^{99m}$-Tc-DTPA-PLL.

(Fab)$_2$ fragments of the following antibodies were generated by pepsin cleavage: R11D10 mAb, specific for heart myosin; 323 mAb, specific for human breast cancer; and goat anti-mouse mAb, specific for murine IgG. Prior to coupling, the (Fab)$_2$ fragments were reduced into free SH-containing Fab' fragments by treatment with DTT. Fab' fragments were conjugated to labelled chelating polymers by incubation at pH 8.0 for 30–60 min at 20° C. Free antibody and polymer were separated by HPLC or chromatography on BioGel 0.5 m. FIG. 4 shows separation of the reaction mixture using HPLC chromatography monitored by optical density and by $^{99m}$Tc radioactivity. The successful formation of the conjugate is evident. The specific activity of the labelled antibody or protein is in the range of 20 to greater then 100 $\mu$Ci/$\mu$g of protein, depending on the molecular weight of the chelating polymer used. No non-specific binding of reduced $^{99m}$-Tc to the polymer loaded with cold metal was found.

The approach described above takes advantage of the very rapid coupling between sulfhydryl and maleimido groups and absence of non-specific binding of the reduced radio-isotope to the polymer. Constituents of the reaction mixture can react within minutes and then can be promptly separated to produce pure labelled conjugate preventing radioactivity loss, often a problem with rapidly decaying radioisotopes, such as $^{99m}$-Tc.

Figure 5:
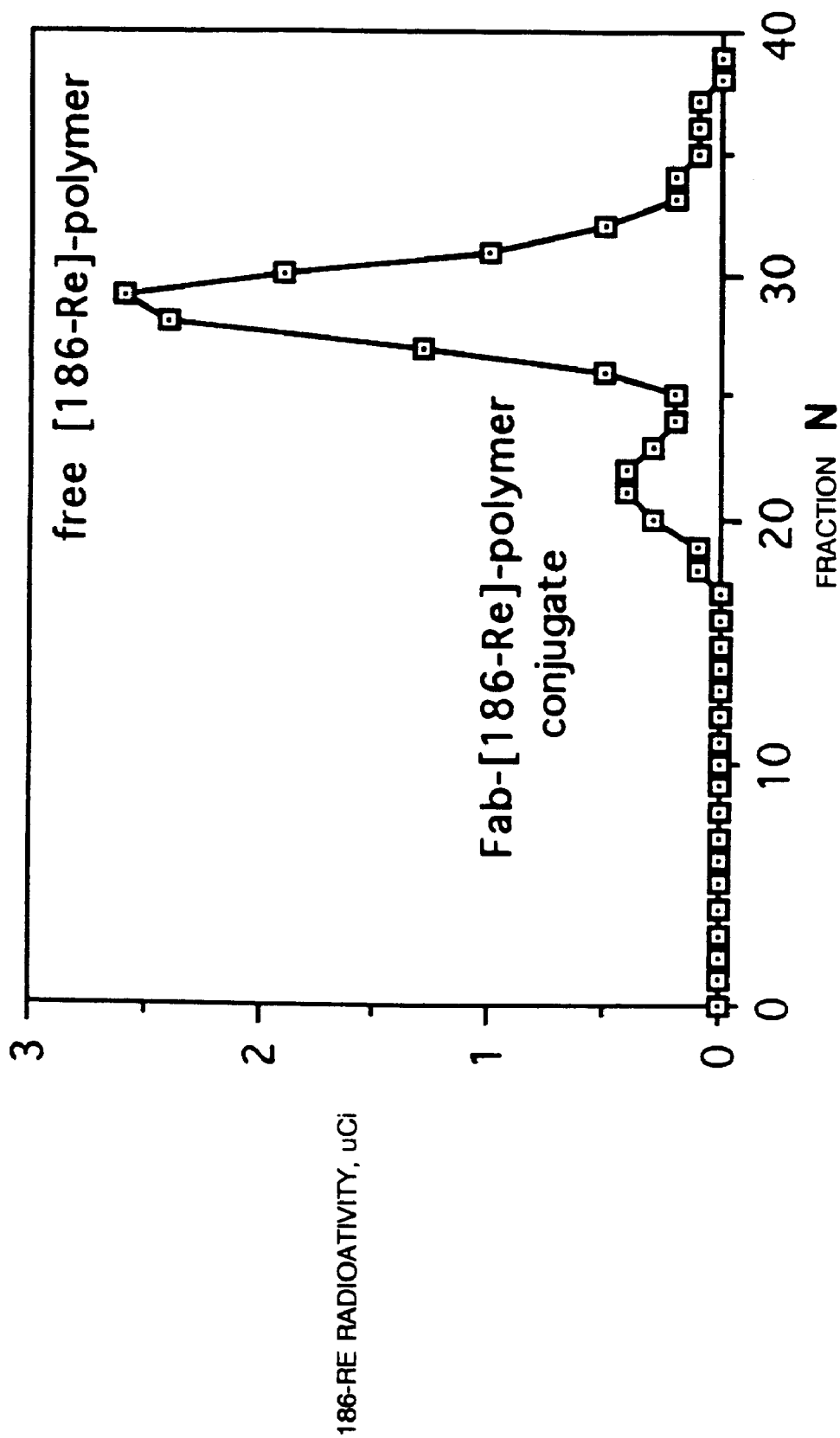
FIG. 5 is a graph showing the chromatographic analysis of the conjugation product between R11D10 Fab' and $^{186}$-Re-DTPA-PLL.

The same approach can be applied to protein labelling with $^{186\ or\ 188}$-Re, which presents the same problems with non-specific metal binding described for $^{99m}$-Tc. FIG. 5 shows the conventional gel filtration separation of a reaction mixture of Fab' fragments and $^{186}$-Re-loaded chelating polymer. The specific activity of the resulting conjugate was 40 $\mu$Ci/$\mu$g of protein.

Proteins labelled in this manner are very stable. The metal is strongly and specifically bound to the polymer, eliminating the problem of non-specifically, weakly-bound metal becoming detached from the protein and transchelating by transferrin in the patient, creating an undesirable background and labelling non-target tissues with radioactivity. The thioether bond between polymer and Fab' moieties is also durable under physiological conditions.

Figure 6:
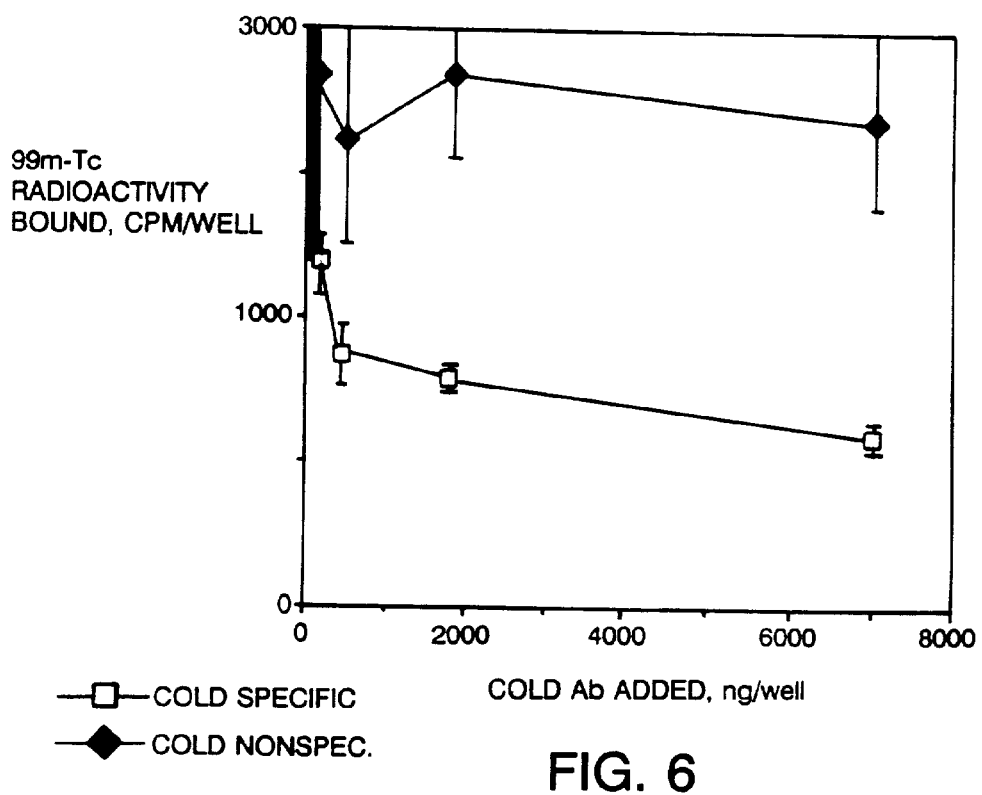
FIG. 6 is a graph showing inhibition of $^{99m}$-Tc-labelled goat anti-mouse IgG binding with antigen by unlabelled antibody.

This method preserves the immunoreactivity and specificity of the labelled antibody. $^{99m}$Tc-labelled immunoconjugates obtained using this protocol retained their antigen binding ability as shown in FIG. 6, depicting the specific inhibition of $^{99m}$-Tc-labelled goat anti-mouse antibody binding to its antigen, murine IgG, in the presence of unlabelled antibody. There was no inhibition observed in the presence of cold non-specific antibody.

Immunoreactivity and specificity of antibody-binding was also tested in vivo. Nude mice with subcutaneously implanted human breast tumor were used for visualization experiments. Mice were injected with $^{111}$-In-labelled mAb 323. A dose of 50 $\mu$Ci of $^{111}$-In activity (approximately 1 $\mu$g of protein) was used per animal. Specific binding was evaluated after 24 h using a gamma-radiation detection system.

Figure 7:
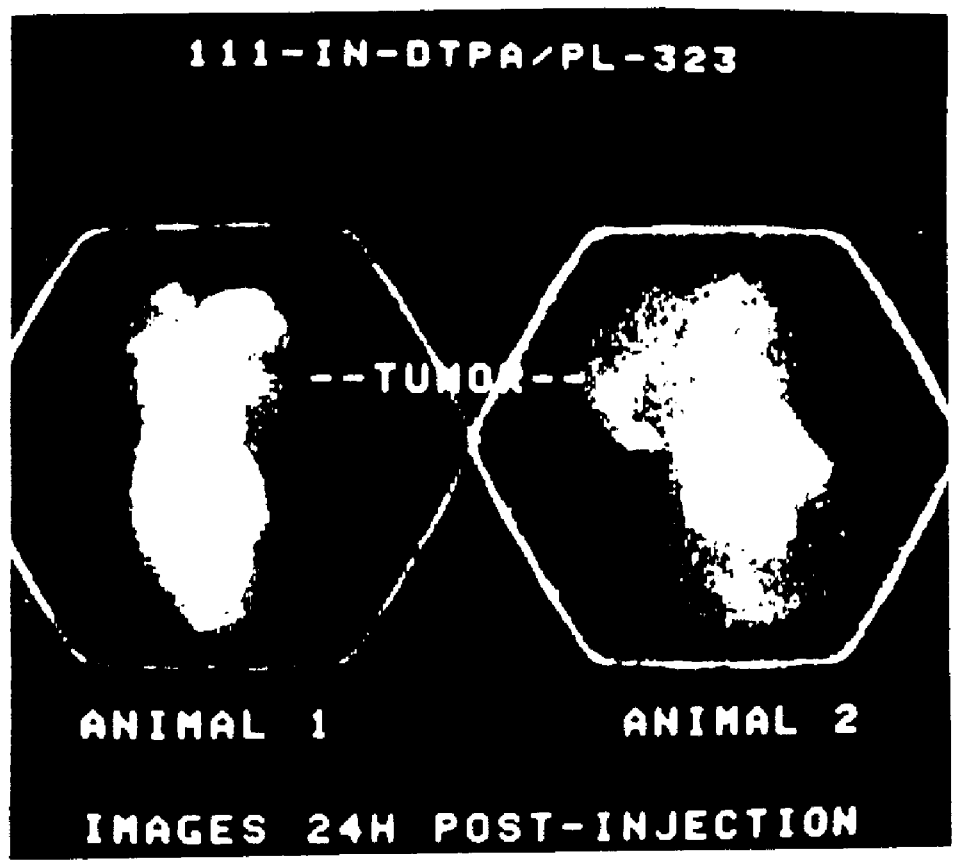
FIG. 7 is a photograph of a tumor visualized in mice using $^{111}$-In-labelled mAb 323 Fab'.

Targeted accumulation of radiolabelled immunoconjugates was observed in nude mice bearing human breast tumor implants, as shown in FIG. 7. After 24 h, the accumulation of mAb 323-conjugated $^{111}$-In radioactivity in the tumor was high enough for diagnostic and therapeutic purposes.

What is claimed is:

1. A method for labelling a protein with a metal comprising:
   (a) providing a synthetic polypeptide to which a metal is chelated, said polypeptide having a molecular weight of at least 1,000 daltons, being purified from unchelated metal, and comprising a reactive group;
   (b) providing a protein comprising a sulfhydryl group which is either naturally occurring in said protein or the product of chemical modification; and
   (c) reacting said polypeptide with said protein to form a covalent bond at a single site therebetween via said reactive group and said sulfhydryl group to yield a metallically-labelled protein substantially free of unchelated metal.

2. The method of claim 1, wherein said metal is a radioisotope.

3. The method of claim 1, wherein said metal is paramagnetic.

4. The method of claim 1, wherein said metal is chelated at multiple sites to said polypeptide.

5. The method of claim 1, wherein said polypeptide is poly-L-lysine.

6. The method of claim 1, wherein said reactive group is a thiol-reactive group.

7. The method of claim 6, wherein said thiol-reactive group is a maleimido group.

8. The method of claim 1, wherein said protein is an antibody.

9. The method of claim 8, wherein said antibody is an monoclonal antibody.

10. The method of claim 9, wherein said monoclonal antibody is an Fab' fragment.

11. A method of making a metallically-labelled complex having a molecular weight of at least 1,000 daltons, said method comprising:
   (a) providing a synthetic polypeptide, comprising a reactive group, which polypeptide covalently bonds to a protein at a single site via said reactive group, and further comprising a chelating group; and
   (b) contacting the polypeptide of (a) with a metal to cause chelation therewith.

12. The method of claim 11, wherein said metal is a radioisotope.

13. The method of claim 11, wherein said polypeptide is a poly-L-lysine.

14. The method of claim 11, wherein said reactive group is a thiol-reactive group.

15. The method of claim 14, wherein said thiol-reactive group is a maleimido group.

16. The method of claim 11, wherein said chelating group is at multiple sites.

17. The method of claim 16, wherein said chelating group is DTPA.

18. A synthetic polypeptide to which a metal is chelated, having a molecular weight of at least 1,000 daltons, being purified from unchelated metal, comprising a reactive group, which polypeptide covalently bonds to a protein at a single site via said reactive group.

19. The polypeptide of claim 18, wherein said metal is a radioisotope.

20. The polypeptide of claim 18, wherein said protein is an antibody.

21. The polypeptide of claim 20, wherein said antibody is an monoclonal antibody.

22. The polypeptide of claim 21, wherein said monoclonal antibody is an Fab' fragment.

23. A metal-labelled complex, comprising a synthetic polypeptide to which a metal is chelated, having a molecular weight of at least 1,000 daltons, being purified from unchelated metal, and being covalently bonded to a protein at a single site, said protein having substantially no unchelated metal associated therewith.

24. The complex of claim 23, wherein said metal is a radioisotope.

25. The complex of claim 23, wherein said protein is an antibody.

26. The complex of claim 25, wherein said antibody is an monoclonal antibody.

27. The complex of claim 26, wherein said monoclonal antibody is an Fab' fragment.

28. A method of labelling cells in a mammal, comprising administering to a mammal the compound of claim 23, wherein said protein specifically binds to said cells.

29. The method of claim 28, wherein said metal is Gd.

30. The method of claim 28, wherein said metal is a radioisotope.

31. The method of claim 30, wherein said radioisotope is $^{111}$-In.

32. The method of claim 30, wherein said radioisotope is $^{99m}$-Tc.

33. A method of killing unwanted cells in a mammal, said method comprising administering to a mammal the compound of claim 24, wherein said radioisotope is cytotoxic, and wherein said protein specifically binds to said cells.

34. The method of claim 33, wherein said tissue is a tumor.

35. The method of claim 33, wherein said radioisotope is $^{186}$-Re.

36. The method of claim 33, wherein said radioisotope is $^{188}$-Re.

* * * * *